(12) United States Patent
Nakatsuka

(10) Patent No.: US 6,512,068 B1
(45) Date of Patent: Jan. 28, 2003

(54) ADHESIVE COMPOSITION AND METHOD FOR PRODUCING IT

(75) Inventor: Kazumitsu Nakatsuka, Kurashiki (JP)

(73) Assignee: Kuraray Co., Ltd., Kurashiki (JP)

( * ) Notice: Subject to any disclaimer, the term of this patent is extended or adjusted under 35 U.S.C. 154(b) by 106 days.

(21) Appl. No.: 09/583,767

(22) Filed: May 31, 2000

(30) Foreign Application Priority Data

May 31, 1999 (JP) ............................................ 11-152131

(51) Int. Cl.⁷ .............................................. C08F 130/02
(52) U.S. Cl. ........................ 526/277; 526/274; 526/286; 526/287; 526/318.2; 526/318.3
(58) Field of Search ................................ 526/274, 277, 526/286, 287, 318.2, 318.3

(56) References Cited

FOREIGN PATENT DOCUMENTS

| DE | 199 18 974 | 12/1999 |
|----|------------|---------|
| EP | 0 074 708  | 3/1983  |
| EP | 0 115 948  | 8/1984  |
| EP | 0 661 034  | 7/1995  |
| EP | 0 712 622  | 5/1996  |
| JP | 62-223289  | 2/1987  |
| JP | 1-113057   | 5/1989  |
| JP | 06093211   | 5/1994  |
| JP | 10251115   | 9/1998  |

OTHER PUBLICATIONS

Patent Abstracts of Japan, vol. 016, No. 128 (C–0924), Apr. 2, 1992, JP 03 294286, Dec. 25, 1991.

*Primary Examiner*—Helen L. Pezzuto
(74) *Attorney, Agent, or Firm*—Oblon, Spivak, McClelland, Maier & Neustadt, P.C.

(57) ABSTRACT

Provided are a substantially transparent adhesive composition for hard tissue, and a method for producing it; the adhesive composition exhibits good adhesiveness to hard tissue, especially to both enamel and dentin, and has the advantage of improved bonding durability especially in water; this contains (a) a substantially water-insoluble, acid group-containing polymerizable monomer which has, in the molecule, at least one hydrocarbon group selected from an alkylene group having from 8 to 25 carbon atoms, an alkyl group having from 8 to 25 carbon atoms and an aromatic group, and/or its salt, and (b) water, and has pH of from 1.0 to 6.0.

21 Claims, No Drawings

ADHESIVE COMPOSITION AND METHOD FOR PRODUCING IT

BACKGROUND OF THE INVENTION

1. Field of the Invention

The present invention relates to an adhesive composition for hard tissue, which exhibits good adhesiveness to hard tissue such as bones, nails, teeth and others, of humans and animals. More precisely, it relates to an adhesive composition for dental use, which is for bonding restorative dental materials, especially dental resin materials such as dental bonding materials, dental cement materials, composite resins for dental restoration, compomers for dental restoration and the like, to teeth in dental treatment.

2. Description of the Related Art

For restoration of teeth damaged by caries or the like, generally used are restorative dental materials such as restorative composite resins, restorative compomers, etc. However, such restorative dental materials are not adhesive by themselves. In general, therefore, ordinary dental restoration comprises pre-treating the surface of a tooth with a strong acid etchant such as phosphoric acid or the like, then applying a bonding material to the etched surface of the tooth, and bonding a restorative material to the tooth via the bonding material. However, the method using such an acid etchant requires washing the etched tooth with water to completely remove the strong acid from the tooth followed by drying the tooth. This method is defective because the post-etching treatment is complicated. Further the dental bonding system using the acid etchant could ensure good adhesiveness to tooth enamel but could not to dentin.

To solve the problems, a dental bonding system using a self-etching primer has been proposed in Japanese Patent Laid-Open No. 223289/1987, in which, briefly, a tooth is pre-treated with a self-etching primer that comprises an acid (including acid monomers) and a hydrophilic monomer and not with an acid etchant, and a bonding material is directly applied to the pre-treated tooth not washed with water. In the system, the adhesiveness of the bonding material to dentin could be improved in some degree. However, since the primer contains a hydrophilic monomer in large quantities, the monomer penetrates into a tooth and the resin layer formed through polymerization and curing of the primer on the tooth could not be sufficiently waterproof. As a result, the resin layer or hybrid layer could not be sufficiently adhesive to the tooth for a long period of time. In the above reference 223289/1987, disclosed is a bonding durability test of testing bonded tooth pieces for their bonding durability by immersing them in water at 45° C. for 5 days. The test results indicate bonding durability in some degree of the tooth pieces bonded with a primer that contains a hydrophilic monomer such as 2-hydroxyethyl methacrylate (HEMA) and the like in large quantities. However, even the primer that could ensure the bonding strength in the bonding durability test is still problematic in actual dental use, since its cured layer is often degraded while in the mouth for a long period of time. As a result, the restorative material bonded to a tooth via the hybrid layer will peel off since water will leak in the bonded interface. In that situation, it is further desired a technique of further improving the bonding durability of restorative materials to teeth.

In Japanese Patent Laid-Open No. 113057/1989, proposed is a primer comprising water, a water-soluble polymerizable monomer and a salt of an acid. The laid-open specification says that the primer containing a salt of an acid and not an acid itself could exhibit improved adhesiveness to dentin. However, there is no description in the above reference relating to the bonding strength of a self-etching primer to enamel, which is the most important parameter of that primer. In this connection, it has been found that the bonding strength to enamel of the primer described in the Examples of the laid-open specification of the above reference is extremely low. Accordingly, from the primer proposed in 113057/1989, a self-etching primer with strong adhesiveness to both the two types of hard tissue, enamel and dentin, is not completed. In addition, as so mentioned hereinabove with respect to Japanese Patent Laid-Open No. 223289/1987, the primer disclosed in the laid-open specification does not solve the essential problem with it in that its bonding durability is poor since it contains a hydrophilic monomer such as HEMA in large quantities.

In Japanese Patent Laid-Open No. 251115/1998, a primer is disclosed comprising a specific phosphoric acid monomer, a polycarboxylic acid monomer and water. Though not containing a hydrophilic monomer such as HEMA or the like, the primer disclosed could exhibit good adhesiveness to teeth. However, the primer necessarily contains a water-soluble organic solvent so as to uniformly dissolve the constituent ingredients therein, in which, the water-soluble organic solvent is indispensable. If the primer containing a water-insoluble acid monomer dissolved in such a water-soluble organic solvent is intended to penetrate into a tooth, especially into dentin having a large water content, the acid monomer therein will be insolubilized with the tissue fluid in the tooth and therefore could not fully penetrate or diffuse in the tooth. Therefore, the primer is defective in that its bonding strength greatly fluctuates depending on the constituent ingredients. In addition, the organic solvent for the primer includes HEMA, and it is clear that 251115/1998 does not relate to improving the bonding durability of the primer. The primer disclosed was actually tested for its bonding durability. In the test, the bonding strength of the primer samples tested was not uniform and was poor.

Japanese Patent Laid-Open No. 93211/1994, discloses a primer containing a specific phosphate and/or its salt, and water. The laid-open specification of the above reference discloses that the primer composition has good adhesiveness to metals especially to stainless, well bonding thereto. However, in a bonding test with teeth, the primer samples described in the Examples of 93211/1994 did not exhibit high adhesiveness to teeth. In particular, in a bonding durability test with teeth such as thermocycle tests, the bonding strength of the primer samples are noticeably lowered. Accordingly, the primer disclosed in 93211/1994 is not suitable for dental treatment.

SUMMARY OF THE INVENTION

The subject matter of the present invention is to provide an adhesive composition for hard tissue which is effective for improving the adhesiveness between hard tissue, especially teeth (enamel, dentin, cementum) and dental resin materials, for example, dental bonding materials, dental resin cements, dental glass ionomer cements, restorative dental composite resins, restorative dental compomers and the like, especially for improving the bonding durability of such dental resin materials to teeth in water.

The adhesive composition of the present invention must satisfy the following requirements (1) to (5):

(1) The adhesive composition must be able to decalcify the smeared layer that may be formed in cutting teeth with a cutting tool such as a cutting turbine, a cutting laser or the like, in order that it can satisfactorily exhibit its good adhesiveness to a tooth.

(2) The adhesive composition must contain a substantially water-insoluble, acid group-containing polymerizable monomer with good waterproofness, as an indispensable ingredient, in order that it can ensure good adhesiveness to a tooth and good tooth-bonding durability, where the phrase "substantially water insoluble" is used in the present application to mean a water solubility of at most 5% by weight at 25° C.

(3) The substantially water-insoluble, acid group-containing polymerizable monomer in the adhesive composition must be solubilized in water, and the adhesive composition must contain water as another indispensable ingredient, in order that the monomer can easily penetrate into a tooth that contains water.

(4) The solubilized, acid group-containing polymerizable monomer must be adhesive to a tooth.

(5) The solubilized, acid group-containing polymerizable monomer must be able to bond to hydroxyapatite and others in the tooth, and must be polymerized and cured with a polymerization catalyst present in the adhesive composition or while the bonding material, composite resin, resin cement or the like having been applied onto the adhesive composition is cured.

It was found that an aqueous composition that contains a particular, solubilized, acid group-containing polymerizable monomer can exhibit improved bonding durability which is much better than that expected from conventional bonding compositions. On the basis of this finding, I have completed the present invention.

Specifically, the invention is to provide a substantially transparent adhesive composition containing (a) a substantially water-insoluble, acid group-containing polymerizable monomer which has, in the molecule, at least one hydrocarbon group selected from an alkylene group having from 8 to 25 carbon chains, an alkyl group having from 8 to 25 carbon chains and an aromatic group, and/or its salt, and (b) water, and having a pH of from 1.0 to 6.0.

Another aspect of the invention is to provide a method for producing a substantially transparent adhesive composition, which comprises mixing (a) a substantially water-insoluble, acid group-containing polymerizable monomer which has, in the molecule, at least one hydrocarbon group selected from an alkylene group having from 8 to 25 carbon chains, an alkyl group having from 8 to 25 carbon chains and an aromatic group, (b) a basic compound capable of forming a soluble salt with the acid group-containing polymerizable monomer, and (c) water to thereby give a mixture having a pH of from 1.0 to 6.0.

DESCRIPTION OF THE PREFERRED EMBODIMENTS

The substantially water-insoluble, acid group-containing polymerizable monomer for use in the invention has at least one hydrocarbon group selected from an alkylene group having from 8 to 25 carbon atoms, an alkyl group having from 8 to 25 carbon atoms and an aromatic group, as so mentioned hereinabove, and has an acid group such as a phosphoric acid group, a pyrophosphoric acid group, a thiophosphoric acid group, a carboxylic acid group, a sulfonic acid group or the like, and additionally a polymerizable unsaturated group such as an acryloyl group, a methacryloyl group, a vinyl group, a styrene group or the like, and its solubility in water at 25° C. is at most 5%, preferably at most 1%. Specific examples of the substantially water-insoluble, acid group-containing polymerizable monomer are mentioned below. Of the monomers to be mentioned below, preferred are those having an unsaturated group of a methacryloyl or acryloyl group. The expression "(meth) acryl" referred to herein is meant to include both "methacryl" and "acryl".

The phosphoric acid group-containing polymerizable monomer includes, for example, 8-(meth)acryloyloxyoctyl dihydrogenphosphate, 9-(meth)acryloyloxynonyl dihydrogenphosphate, 10-(meth)acryloyloxydecyl dihydrogenphosphate, 11-(meth)acryloyloxyundecyl dihydrogenphosphate, 12-(meth)acryloyloxydodecyl dihydrogenphosphate, 16-(meth)acryloyloxyhexadecyl dihydrogenphosphate, 20-(meth)acryloyloxyeicosyl dihydrogenphosphate, di(meth)acryloyloxyoctyl hydrogenphosphate, di(meth)acryloyloxynonyl hydrogenphosphate, di(meth)acryloyloxydecyl hydrogenphosphate, 2-(meth)acryloyloxyethylphenyl hydrogenphosphate, 2-(meth)acryloyloxyethyl(2'-bromooctyl) hydrogenphosphate, 2-(meth) acryloyloxyethyloctyl hydrogenphosphate, 2-(meth) acryloyloxyethylnonyl hydrogenphosphate, 2-(meth) acryloyloxyethyldecyl hydrogenphosphate, 2-(meth) acryloyloxybutyldecyl hydrogenphosphate, (meth) acryloyloxyethylphenyl phosphonate, etc.; (8-methacryloxy)octyl-3-phosphonopropionate, (9-methacryloxy)nonyl-3-phosphonopropionate, (10-methacryloxy)decyl-3-phosphonopropionate, (8-methacryloxy)octyl-3-phosphonoacetate, (10-methacryloxy)decyl-3-phosphonoacetate and others such as those described in Japanese Patent Laid-Open No. 294286/1991; 2-methacryloyloxyethyl(4-methoxyphenyl) hydrogenphosphate, 2-methacryloyloxypropyl(4-methoxyphenyl) hydrogenphosphate and others such as those described in Japanese Patent Laid-Open No. 281885/1987; as well as water-insoluble, phosphoric acid group-containing polymerizable monomers having an alkylene group with from 8 to 20 carbon chains, an alkyl group with from 8 to 20 carbon chains, or an aromatic group, such as those exemplified in Japanese Patent Laid-Open Nos. 113089/1977, 67740/1978, 69494/1978, 144939/1978, 128393/1983 and 192891/1983, and their acid chlorides.

The pyrophosphoric acid group-containing polymerizable monomer includes, for example, di(8-(meth) acryloyloxyoctyl) pyrophosphate, di(9-(meth) acryloyloxynonyl) pyrophosphate, di(10(meth) acryloyloxydecyl) pyrophosphate, di(12-(meth) acryloyloxydodecyl) pyrophosphate, etc. and their acid chlorides.

The thiophosphoric acid group-containing polymerizable monomer includes, for example, 8(meth)acryloyloxyoctyl dihydrogendithiophosphate, 9-(meth)acryloyloxynonyl dihydrogendithiophosphate, 10-(meth)acryloyloxydecyl dihydrogenthiophosphate, etc., and their acid chlorides.

The carboxylic acid group-containing polymerizable monomer includes, for example, 4-(meth) acryloyloxyethyloxycarbonylphthalic acid, 4-(meth) acryloyloxybutyloxycarbonylphthalic acid, 4-(meth) acryloyloxyhexyloxycarbonylphthalic acid, 4-(meth) acryloyloxyoctyloxycarbonylphthalic acid, 4-(meth) acryloyloxydecyloxycarbonylphthalic acid, and their acid anhydrides; 8-(meth)acryloylaminooctylcarboxylic acid, 9-(meth)acryloyloxy-1,1-nonane-dicarboxylic acid, 10-(meth)acryloyloxy-1,1-decane-dicarboxylic acid, 1,1-(meth)acryloyloxy-1,1-undecane-dicarboxylic acid, etc., and their acid chlorides.

The sulfonic acid group-containing polymerizable monomer includes, for example, sulfonic acid group-containing compounds such as 8-(meth)acrylamidooctylsulfonic acid, 10-(meth) acrylamidodecylsulfonic acid, styrenesulfonic acid, etc.

Most preferred are di-acidic or higher polyacidic polymerizable monomers, of which the salts formed with basic compounds are still acidic and are solubilized in water. Di-acidic or higher poly-acidic polymerizable monomers referred to herein are meant to include polymerizable monomers having at least two acid groups in the molecule, and polymerizable monomers having at least one polyacidic group such as a di-phosphoric acid group in the molecule, and their salts formed with an equimolar amount of monovalent basic compounds are still acidic. The above-mentioned, phosphoric acid group-containing polymerizable monomers are especially preferred, as having good adhesiveness and bonding durability even to enamel and dentin. One or more of these specific structure-having, substantially water-insoluble, acid group-containing polymerizable monomers can be used herein either singly or as combined.

In the invention, the substantially water-insoluble, acid group containing polymerizable monomer is formed into a water soluble salt with a basic compound, and the penetrability into a tooth of its salt and the bonding strength thereof to a tooth are both improved. The basic compound for use in the invention must form a water-soluble salt with the substantially water-insoluble, acid group-containing polymerizable monomer, and is so selected that the solubility in water at 25° C. of its salt with the acid group-containing polymerizable monomer is at least 5%, preferably at least 10% by weight. In the adhesive composition of the invention, the salt exists mostly in the form of a combination of an anion derived from the acid group-containing polymerizable monomer and a cation derived from the basic compound. Preferred examples of the basic compound include alkali metal hydroxides such as sodium hydroxide, lithium hydroxide, potassium hydroxide, etc.; strongly basic acid derivatives composed of an alkali metal and a weak acid having pKa of at least 3, such as sodium carbonate, sodium hydrogencarbonate, potassium carbonate, potassium hydrogencarbonate, lithium carbonate, lithium hydrogencarbonate, sodium formate, sodium benzoate, sodium hydrogenoxalate, sodium acetate, potassium acetate, sodium propionate, sodium borate, sodium dihydrogenphosphite, potassium dihydrogenphosphite, sodium dihydrogenphosphate, potassium dihydrogenphosphate, disodium hydrogenphosphate, dipotassium hydrogenphosphate, etc; and an amine, etc.

The amine may be any of primary amine, secondary amine and tertiary amine, any of which may be selected for the substantially water-insoluble, acid group-containing polymerizable monomers for use in the invention, depending on the type of the monomers. For example, preferred is a triethanolamine, diethanolamine, 2-dimethylaminoethyl (meth)acrylate, 3-dimethylaminopropyl (meth)acrylate, 4-dimethylaminobutyl (meth)acrylate, 6-dimethylaminohexyl (meth)acrylate, 10-dimethylaminodecyl (meth)acrylate, 4-(dimethylamino) phenethyl alcohol, 4-(diethylamino) phenethyl alcohol, 4-(dipropylamino)phenethyl alcohol, N,N-(2-hydroxyethyl)-p-toluidine, N,N-(2-hydroxypropyl)-p-toluidine, diethyl-p-toluidine, dipropyl-p-toluidine, dibutyl-p-toluidine, diethoxyethyl-p-toluidine, dibutoxyethyl-p-toluidine, di(polyoxyethylene)oxyethyl-p-toluidine, hexamethylenediamine, aqueous dimethylamine, pentamethylenediamine, diethylamine, ethylenediamine, 2-aminoethanol, triethylamine, 2-dimethylaminoethanol, etc.

Preferably, the amine is so selected that a gel composition containing 0.047 mols of a substantially water-insoluble, di-phosphoric acid group-containing polymerizable monomer, 10-methacryloyloxydecyl dihydrogenphosphate (hereinafter referred to as MDP) in 85 g of distilled water can be formed into a transparent aqueous composition when 0.047 mols of the amine is added thereto.

The "substantially transparent" composition is meant to indicate a composition which is macroscopically transparent with neither deposits nor floating solids or with no cloudiness at 25° C. The amines mentioned above will include amines capable of serving as a polymerization initiator or a reducing agent that will be mentioned hereinunder. I have confirmed that the amines having the catalytic capability can still exhibit its polymerization-initiating capability and reducing capability even after formed into salts with the acid group-containing polymerizable monomers. One or more of these basic salts can be used herein either singly or as combined.

The amount of the basic compound to be combined with the substantially water-insoluble, acid group-containing polymerizable monomer is not specifically defined, so far as it can solubilize the monomer in water. As so mentioned hereinabove, however, the adhesive composition of the invention must be so controlled that its pH falls between 1.0 and 6.0, in order that it can decalcify the smeared layer that may be formed in cutting a tooth with a cutting tool such as a cutting laser or the like, and can exhibit increased adhesiveness to the tooth, especially to the enamel. If the pH of the adhesive composition is larger than 6, a small amount of an acid serving as a pH controlling agent shall be added to the composition to thereby reduce the pH of the resulting composition to at most 6. The acid serving as such a pH controlling agent may be any of inorganic acids or organic acids, but is preferably an organic acid such as acetic acid, maleic acid, citric acid, methacrylic acid or the like having no influence on teeth.

The pKa value of the acid usable herein as a pH controlling agent must be larger than that of the substantially water-insoluble, acid group-containing polymerizable monomer to be in the adhesive composition of the invention. If an acid, of which the pKa value is smaller than that of the substantially water-insoluble, acid group-containing polymerizable monomer, is added as a pH controlling agent to the adhesive composition, the substantially water-soluble salt of the substantially water-insoluble, acid group-containing polymerizable monomer existing in the composition will undergo salt exchange with the acid of the pH controlling agent, whereby the substantially water-insoluble, acid group-containing polymerizable monomer is dissociated from the salt to be in its free form in the composition. If so, the composition could not be transparent. Most acids usable as the pH controlling agents are soluble in water. Therefore, the acid added to the composition will dissolve in water after the composition has been applied to a tooth and cured thereon, whereby the bonding durability of the cured composition will lower. Accordingly, it is desirable that the amount of the acid to be in the composition is as small as possible, and must be generally at most 10% by weight, preferably at most 5% by weight of the composition.

The total amount of the acid group-containing polymerizable monomer and its salt to be in the adhesive composition of the invention may fall generally between 1% by weight and 80% by weight, preferably between 5% by weight and 50% by weight, more preferably between 15 by weight and 30% by weight. If the amount is smaller than 1 by weight or larger than 80% by weight, the bonding strength of the composition will be low. In general, a minor amount of the substantially water-insoluble, acid group-containing polymerizable monomer is present in the composition in the form of its free acid and not in the form of its salt. The amount of the free acid monomer existing in the composition is controlled by the solubility of the substantially water-insoluble, acid group-containing polymerizable monomer in water and in the salt of the monomer.

Water to be in the adhesive composition of the invention must be substantially free from impurities that may have negative influence on the bonding strength between a tooth and a restorative dental material applied thereto. Preferred is distilled water or ion-exchanged water. The amount of water in the composition may fall generally between 1% by weight and 99% by weight, but preferably between 10% by weight and 95% by weight, more preferably between 30% by weight and 90% by weight.

In case where the adhesive composition is, after applied onto the surface of a tooth, dried up with a dental air syringe or the like to form an extremely thin layer on the tooth, a polymerization initiator is not always necessary therein. However, if a dental operator applies an extremely large amount of the adhesive composition onto a tooth, it will be difficult for the composition cure because of the difficulty in drying. If so, the bonding strength of the cured composition will be low. Therefore, it is desirable to add a polymerization initiator to the adhesive composition. The polymerization initiator may be any of known photopolymerization initiators and/or autocure polymerization initiators. The photopolymerization initiators include, for example, a-diketones, ketals, thioxanthones, acylphosphine oxides, coumarins, halomethyl-substituted s-triazine derivatives, etc.

Examples of α-diketones are camphorquinone, benzil, 2,3-pentanedione, etc; Examples of ketals are benzyldimethyl ketal, benzyldiethyl ketal, etc. Examples of thioxanthones are 2-chlorothioxanthone, 2,4-diethylthioxanthone, etc.

Examples of acylphosphine oxides are 2,4,6-trimethylbenzoyldiphenylphosphine oxide, 2,6-dimethoxybenzoyldiphenylphosphine oxide, 2,6-dichlorobenzoyldiphenylphosphine oxide, 2,3,5,6-tetramethylbenzoyldiphenylphosphine oxide, benzoyl-di-(2,6-dimethylphenyl) phosphonate, 2,4,6-trimethylbenzoylethoxyphenylphosphine oxide, salts of 2,4,6-trimethylbenzoylphenylphosphinic acids; as well as water-soluble acylphosphine oxide compounds and others such as those disclosed in Japanese Patent Publication No. 57916/1991.

Examples of coumarins are 3,3'-carbonyl-bis(7-diethylamino)coumarin, 3-(4-methoxybenzoyl)coumarin, 3-thienoylcoumarin and others such as those described in Japanese Patent Laid-Open No. 245525/1998. Examples of halomethyl-substituted s-triazine derivatives are 2,4,6-tris(trichloromethyl)-s-triazine, 2,4,6-tris(tribromomethyl)-s-triazine, 2-methyl-4,6-bis(trichloromethyl)-s-triazine and others such as those described in Japanese Patent Laid-Open No. 245525/1998. Where the composition is cured through photopolymerization with UV exposure, preferably used are benzoin alkyl ethers, benzyldimethyl ketal, etc. One or more of these photopolymerization initiators may be used herein either singly or as combined. The amount of the photopolymerization initiator to be in the adhesive composition may fall generally between 0.01% by weight and 5% by weight, more preferably between 0.1 and 1% by weight.

The photopolymerization initiator may be used alone, but is generally combined with a reducing agent for enhancing the photocurability of the adhesive composition. The reducing agent includes, for example, tertiary amines, aldehydes, thiol group-having compounds, etc. Examples of tertiary amines are 2-dimethylaminoethyl methacrylate, N,N-bis[(meth)acryloyloxyethyl]-N-methylamine, ethyl 4-dimethylaminobenzoate, butyl 4-dimethylaminobenzoate, butoxyethyl 4-dimethylaminobenzoate, N-methyldiethanolamine, 4-dimethylaminobenzophenone, etc. Examples of aldehydes are dimethylaminobenzaldehyde, terephthalaldehyde, etc. Examples of thiol group-containing compounds are 2-mercaptobenzoxazole, decanethiol, 3-mercaptopropyltrimethoxysilane, thiobenzoic acid, etc. One or more of these reducing agents may be used herein either singly or as combined. The amount of the reducing agent to be in the adhesive composition may fall generally between 0.01% by weight and 5% by weight, but preferably between 0.05% by weight and 3% by weight, more preferably between 0.1% by weight and 1% by weight of the composition.

The autocure polymerization initiator for use herein is preferably a redox polymerization initiator comprising, for example, an oxidizing agent and a reducing agent. Where such a redox polymerization initiator is used in the adhesive composition of the invention, the composition must be divided into at least two parts which are separately wrapped or packaged and which separately contain either one of the oxidizing agent and the reducing agent for the initiator. However, in practical use of the adhesive composition as combined with any other restorative dental material, such as a dental bonding material, a composite resin, a compomer, a rebase resin, a resin cement, a resin-reinforced glass ionomer cement or the like, at least one of the oxidizing agent and the reducing agent may be added to the restorative dental material, while only one of the oxidizing agent and the reducing agent is in the adhesive composition of the invention. In this case, the adhesive composition may be in one package.

The oxidizing agent includes, for example, organic peroxides such as diacyl peroxides, peroxyesters, dialkyl peroxides, peroxyketals, ketone peroxides, hydroperoxides, etc. Specific Examples include diacyl peroxides include benzoyl peroxide, 2,4-dichlorobenzoyl peroxide, m-toluoyl peroxide, etc. Peroxyesters include, for example, t-butylperoxy benzoate, bis-t-butylperoxy isophthalate, 2,5-dimethyl-2,5-bis(benzoylperoxy)hexane, t-butylperoxy-2-ethyl hexanoate, t-butylperoxyisopropyl carbonate, etc. Dialkyl peroxides include, for example, dicumyl peroxide, di-t-butyl peroxide, lauroyl peroxide, etc. Peroxyketals include, for example, 1,1-bis(t-butylperoxy)-3,3,5-trimethylcyclohexane, etc. Ketone peroxides include, for example, methyl ethyl ketone peroxide, cyclohexanone peroxide, methyl acetacetate peroxide, etc. Hydroperoxides include, for example, butylhydroperoxide, cumenehydroperoxide, diisopropylbenzene peroxide, etc.

Preferred examples of the reducing agent are aromatic tertiary amines, aliphatic tertiary amines, and sulfinic acids and their salts. Aromatic tertiary amines include, for example, N,N-dimethylaniline, N,N-diethyl-p-toluidine, N,N-dimethyl-m-toluidine, N,N-diethyl-p-toluidine, N,N-dimethyl-3,5-dimethylaniline, N,N-dimethyl-3,4-dimethylaniline, N,N-dimethyl-4-ethylaniline, N,N-dimethyl-4-i-propylaniline, N,N-dimethyl-4-t-butylaniline, N,N-dimethyl-3,5-di-t-butylaniline, N,N-bis(2-hydroxyethyl)-3,5-dimethylaniline, N,N-di(2-hydroxyethyl) p-toluidine, N,N-bis(2-hydroxyethyl)-3,4-dimethylaniline, N,N-bis(2-hydroxyethyl)-4-ethylaniline, N,N-bis(2- hydroxyethyl)-4-i-propylaniline, N,N-bis(2-hydroxyethyl) 4-t-butylaniline. N,N-bis(2-hydroxyethyl)-3,5-di-i-propylaniline, N,N-bis(2-hydroxyethyl)-3,5-di-t-butylaniline, n-butoxyethyl 4-dimethylaminobenzoate, 2-methacryloyloxy)ethyl 4-dimethylaminobenzoate, etc.

Aliphatic tertiary amines include, for example, trimethylamine, triethylamine, N-methyldiethanolamine, N-ethyldiethanolamine, N-n-butyldiethanolamine, N-lauryldiethanolamine, triethanolamine, (2-dimethylamino)ethyl methacrylate, N-methyldiethanolamine dimethacrylate, N-ethyldiethanolamine dimethacrylate, triethanolamine monomethacrylate, triethanolamine dimethacrylate, triethanolamine trimethacrylate, etc.

Sulfinic acids and their salts include, for example, benzenesulfinic acid, sodium benzenesulfinate, potassium benzenesulfinate, calcium benzenesulfinate, lithium benzenesulfinate, toluenesulfinic acid, sodium toluenesulfinate, potassium toluenesulfinate, calcium toluenesulfinate, lithium toluenesulfinate, 2,4,6-trimethylbenzenesulfinic acid, sodium 2,4,6-trimethylbenzenesulfinate, potassium 2,4,6-trimethylbenzenesulfinate, calcium 2,4,6-trimethylbenzenesulfinate, lithium 2-4,6-trimethylbenzenesulfinate, 2,4,6-triethylbenzenesulfinic acid, sodium 2,4,6-triethylbenzenesulfinate, potassium 2,4, 6-triethylbenzenesulfinate, calcium 2,4,6-triethylbenzenesulfinate, 2,4,6-triisopropylbenzenesulfinic acid, sodium 2,4,6-triisopropylbenzenesulfinate, potassium 2,4,6-triisopropylbenzenesulfinate, calcium 2,4,6-triisopropylbenzenesulfinate, etc. One or more of these oxidizing agents and reducing agents may be used herein either singly or as combined. The amount of these oxidizing agents and reducing agents to be in the adhesive composition may fall generally between 0.01% by weight and 10% by weight, but preferably between 0.05 and 5% by weight, more preferably between 0.1 and 3% by weight of the composition.

The adhesive composition of the invention may optionally contain a hydrophobic polymerizable monomer for improving the curability of the composition and increasing the mechanical strength of the cured composition. Preferably, the hydrophobic polymerizable monomer that may be present in the composition has a solubility in water at 25° C. of at most 5%, more preferably at most 1%. It includes, for example, esters of a-cyanoacrylic acid, (meth) acrylic acid, a-halogenoacrylic acids, crotonic acid, cinnamic acid, sorbic acid, maleic acid, itaconic acid, etc.; (meth)acrylamide and its derivatives; vinyl esters, vinyl ethers, mono-N-vinyl derivatives, styrene derivatives, etc. Of those, preferred are (meth)acrylates, and their examples are mentioned below.

Monofunctional monomers referred to herein are meant to indicate monomers having one olefinic double bond in the molecule.

(a) Monofunctional monomers:

Methyl (meth)acrylate, ethyl (meth)acrylate, isopropyl (meth)acrylate, propyl (meth)acrylate, isobutyl (meth) acrylate, butyl (meth)acrylate, benzyl (meth)acrylate, lauryl (meth)acrylate, 2,3-dibromopropyl (meth)acrylate, 3-methacryloyloxypropyltrimethoxysilane, 11,methacryloyloxyundecyltrimethoxysilane, etc.

(b) Difunctional monomers:

Ethylene glycol di(meth)acrylate, triethylene glycol di(meth)acrylate, propylene glycol di(meth)acrylate, neopentylglycol di(meth)acrylate, 1,6-hexanediol di(meth) acrylate, 1,10-decanediol di(meth)acrylate, bisphenol A diglycidyl(meth)acrylate, 2,2-bis[4-(meth) acryloyloxyethoxyphenyl]propane, 2,2-bis[4-[3(meth) acryloyloxy-2-hydroxypropoxy]phenyl]propane, 1,2-bis[3-(meth)acryloyloxy-2-hydroxypropoxy]ethane, pentaerythritol di(meth)acrylate, 1,2-bis(3-methacryloyloxy-2-hydroxypropoxy)ethane, [2,2,4-trimethylhexamethylenebis(2-carbamoyloxyethyl)] dimethacrylate, etc.

(c) Trifunctional or higher polyfunctional monomers:

Trimethylolpropane tri(meth)acrylate, trimethylolethane tri(meth)acrylate, tetramethylolmethane tri(meth)acrylate, pentaerythritol tetra(meth)acrylate, N,N'-(2,2,4-trimethylhexamethylene)bis[2-(aminocarboxy)propane-1,3-diol] tetramethacrylate, 1,7-diacryloyloxy-2,2,6,6-tetraacryloyloxymethyl-4-oxyheptane, etc.

One or more of these hydrophobic polymerizable monomers may be used herein either singly or as combined. The amount of the hydrophobic polymerizable monomer to be in the adhesive composition may be generally at most 30% by weight, but preferably at most 20% by weight of the composition. If over 30% by weight, the bonding strength of the adhesive composition to dentin will be low.

A small amount of a water-soluble, volatile organic solvent may be added to the adhesive composition, for the purpose of promoting the dissolution of the above-mentioned polymerization initiator and hydrophobic polymerizable monomer in the composition. The water-soluble, volatile organic solvent for that purpose generally has a boiling point at normal pressure of not higher than 150° C., preferably not higher than 100° C. Preferred examples are ethanol, methanol, 1-propanol, isopropyl alcohol, acetone, methyl ethyl ketone, 1,2-dimethoxyethane, 1,2-diethoxyethane, tetrahydrofuran, etc. One or more of these water-soluble, volatile organic solvents may be used herein either singly or as combined. The amount of the water-soluble, volatile organic solvent to be in the adhesive composition is generally at most 20% by weight, but preferably at most 10% by weight, more preferably at most 5% by weight. If over 20% by weight, the adhesiveness to dentin of the composition will fluctuate to a great extent. It is desirable that the water-soluble, volatile organic solvent, if any, in the adhesive composition is removed after the composition has been applied to a tooth, in order not to detract from the adhesiveness of the cured composition. For removing the solvent, for example, employed is a dental air syringe or the like.

If desired, the adhesive composition of the invention may contain a polymerization inhibitor, a colorant, a fluorescent agent, a UV absorbent, etc. Also if desired, a small amount of a hydrophilic polymerizable monomer such as 2-hydroxyethyl methacrylate (HEMA), 3-hydroxypropyl methacrylate or the like may be added to the adhesive composition for the purpose of promoting the dissolution of the polymerization initiator and the hydrophobic polymerizable monomer in the composition. However, the amount of the hydrophilic polymerizable monomer to be in the adhesive composition must be limited to at most 10% by weight, preferably at most 5% by weight of the composition, so as not to lower the bonding durability of the composition. Optionally, an antibacterial polymerizable monomer containing a cation group such as (meth) acryloyloxydodecylpyridinium bromide, (meth) acryloyloxyhexadecylpyridinium chloride (meth) acryloyloxydecylammonium chloride or the like may be added to the adhesive composition, for the purpose of rendering the composition antibacterial properties. Optionally, any known fluoride compounds capable of releasing fluoride ions, such as sodium fluoride, lithium fluoride, sodium monofluorophosphate, cetylamine hydrogen fluoride or the like may be added to the adhesive composition for the purpose of rendering the composition resistant to acids.

Optionally, a filler may be added to the adhesive composition for controlling the coatability, the fluidity and the mechanical strength of the composition. The filler may be any of organic, inorganic or even composite fillers. The inorganic fillers include, for example, silica, silica-based minerals such as kaolin, clay, mica, etc; and silica-based ceramics and glass additionally containing any of $Al_2O_3$, $B_2O_3$, $TiO_2$, $ZrO_2$, $BaO$, $La_2O_3$, $SrO_2$, $CaO$, $P_2O_5$, etc. Especially preferred are lanthanum glass, barium glass, strontium glass, soda glass, lithium borosilicate glass, zinc glass, fluoroaluminium borosilicate glass, borosilicate glass, bioglass, etc. Also preferred are crystalline quartz, hydroxyapatite, alumina, titanium oxide, yttrium oxide, zirconia, calcium phosphate, barium sulfate, aluminum hydroxide, etc. The organic fillers may be of organic resin, including, for example, polymethyl methacrylate, polymers of polyfunctional methacrylates, polyamides, polystyrenes, polyvinyl chloride, chloroprene rubber, nitrile rubber, styrene-butadiene rubber, etc. Optionally, an inorganic/organic composite fillers may be added to the adhesive composition, which may be prepared by dispersing an inorganic filler in the organic resin, or by coating an inorganic filler with the organic resin.

If desired, the fillers may be previously subjected to surface treatment with any known surface-treating agent such as a silane coupling agent or the like, for the purpose of further improving the dispersibility of the fillers and increasing the mechanical strength of the adhesive composition containing the surface-treated filler. The surface-treating agent includes, for example, vinyltrimethoxysilane, vinyltriethoxysilane, vinyltrichlorosilane, vinyltri(β-methoxyethoxy)silane, γ-methacryloyloxypropyltrimethoxysilane, γ-glycidoxypropyltrimethoxysilane, γ-mercaptopropyltrimethoxysilane, γ-aminopropyltriethoxysilane, etc. One or more of these fillers may be used herein either singly or as combined. The amount of the filler, if any, in the adhesive composition may be generally at most 30% by weight, but preferably at most 10% by weight of the composition. If over 30% by weight, the bonding strength of the adhesive composition will be low. As the filler, preferred is colloidal silica having a mean particle size of from 0.001 to 0.1 $\mu$m.

If containing such a filler, the composition will be cloudy and could not be transparent. However, the characteristic feature of the present invention is to solubilize a substantially water-insoluble, acid group-containing polymerizable monomers with good adhesiveness, in water, and there is no problem with the invention and so far as the adhesive composition that contains the above-mentioned, substantially water-insoluble, acid group-containing polymerizable monomer (a) and water (b) is substantially transparent.

To prepare the adhesive composition of the invention, (a) a substantially water-insoluble, acid group-containing polymerizable monomer, having in the molecule, at least one hydrocarbon group selected from an alkylene group having from 8 to 25 carbon atoms, an alkyl group having from 8 to 25 carbon atoms and an aromatic group, (b) a basic compound capable of forming a soluble salt with the acid group-containing polymerizable monomer, and (c) water are mixed to give a mixture having pH of from 1.0 to 6.0. The composition thus prepared is substantially transparent. The substantially transparent composition means that the composition is not cloudy but clear when macroscopically observed.

The adhesive composition of the invention is used as a pre-treating agent for dental treatment of bonding a bonding agent to a tooth. In general, the composition is first applied to a tooth to be treated, and a bonding agent such as dental bonding material, resin cement, glass ionomer cement, zinc phosphate cement, polycarboxylate cement, silicate cement, or the like is thereafter applied onto the tooth coated with the composition. Without using such a bonding agent, the adhesive composition of the invention is first applied to a tooth, and optionally photo-cured through exposure to light from a light emitter, and thereafter a restorative dental material such as a restorative compomer, a restorative composite resin or the like is immediately applied over the cured composition and cured thereon. In this case, the adhesive composition of the invention functions as a bonding agent. In addition, the composition is also usable as a fissure sealant for pit fissures, a coating agent for root surfaces and neighboring teeth portions, a dentinal canal sealant for relieving hyperesthesia, and also as a bonding agent for these.

The adhesive composition of the invention is applicable to not only teeth but also to crown restorative materials such as metals, ceramics, cured composites, etc. In addition, it may be combined with commercially-available metal primers for dental use, ceramic-bonding primers, acid etchants, tooth cleaners such as hypochlorites, etc.

Preferred embodiments of the invention are described below, which, however, are not intended to restrict the scope of the invention. The meanings of the abbreviations used herein are mentioned below.

Acid Group-containing Polymerizable Monomers

MDP

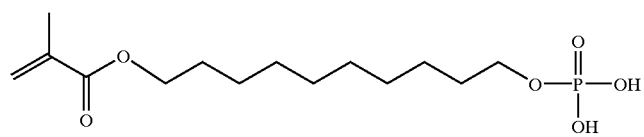

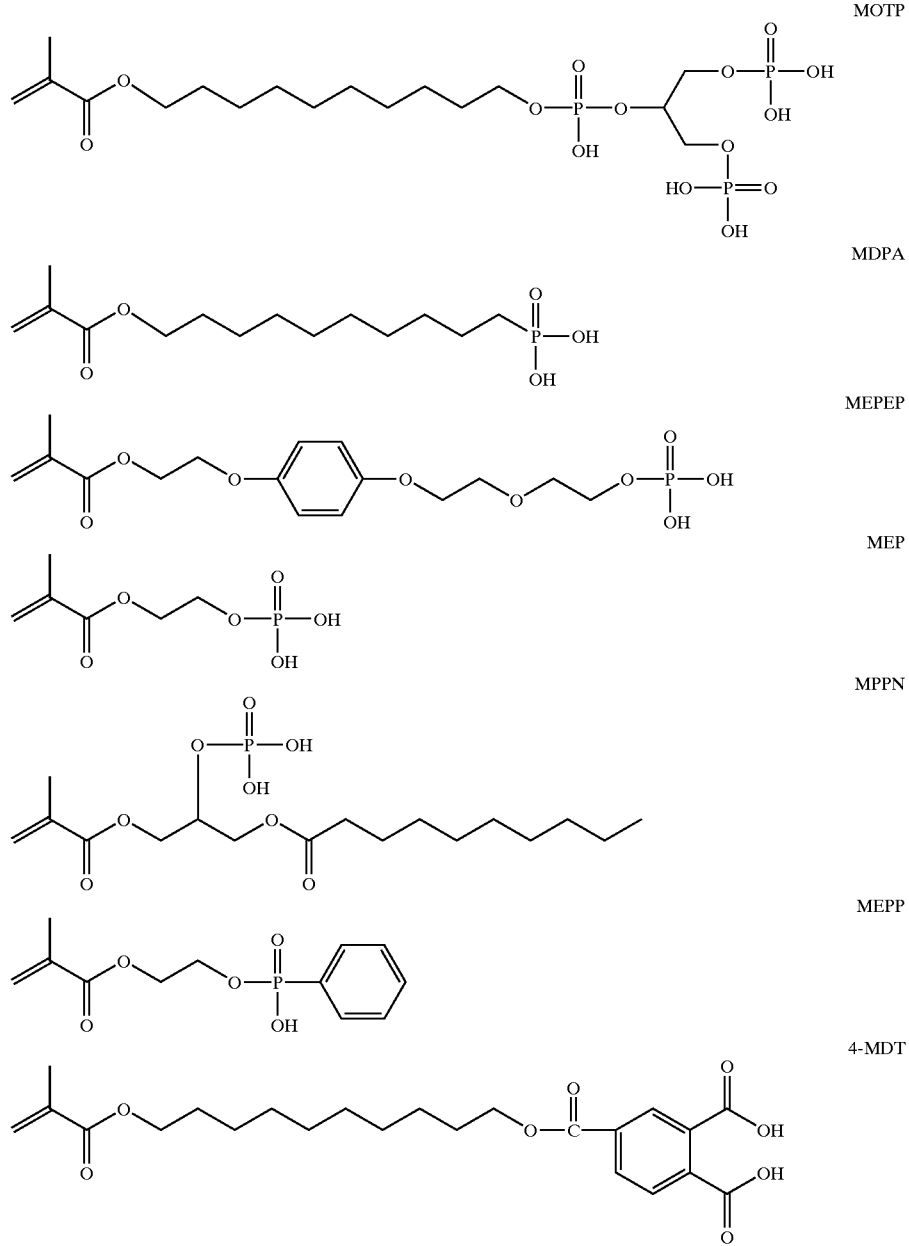

Basic Compounds
  NAOH: solium hydroxide
  KHCO$_3$: potassium hydrogencarbonate
  Na$_2$CO$_3$: solium carbonate
  CaCO$_3$: calcium carbonate
  DET: diethyl-p-toluidine
  DMAP: 4-(dimethylamino)phenethyl alcohol
  DMABAE: ethyl 4-dimethylaminobenzoate
Hydrophilic Polymerizable Monomer
  HEMA: 2-hydroxyethyl methacrylate
Polymerization Initiators, Reducing Agents
  CQ: camphorquinone
  TMPN: sodium 2,4,6-trimethylbenzoylphenylphosphinate
  DMAEMA: dimethylaminoethyl methacrylate
  DMAB: 4-dimethylaminobenzophenone
Polymerization Inhibitor
  BHT: t-butylhydroxytoluene
Polymerizable Monomers
  Bis-GMA: bisphenol A diglycidyl methacrylate
  UDMA: [2,2,4-trimethylhexamethylenebis(2-carbamoyloxyethyl)] dimethacrylate
  9G: poly[ethylene glycol (400)]dimethacrylate Having generally described this invention, a further understanding can be obtained by reference to certain specific examples which are provided herein for purposes of illustration only and are not intended to be limiting unless otherwise specified.

The priority document, Japanese Application 152131 filed May 31, 1999, is incorporated herein by reference in its entirety.

EXAMPLES

Example 1

MDP (15 g, 0.047 mols), distilled water (85 g) and NaOH (1.9 g, 0.047 mols) were mixed to prepare a transparent, aqueous adhesive composition containing sodium salt of MDP. On the other hand, a bonding material comprising Bis-GMA (65 parts by weight), HEMA (35 parts by weight), CQ (1 part by weight) and DMAB (1 part by weight) was prepared. The adhesive composition and the bonding material were tested for the bonding strength, according to the bonding strength test method mentioned below, and the data obtained are given in Table 1.

Bonding Strength Test Method

A bovine anterior tooth was polished in wet with Silicon Carbide papers up #1000-grit (from Nippon Abrasive Paper) to make its surface smooth, then its enamel or dentin was exposed out, and water existing on its surface was blown off with a dental air syringe. An adhesive tape (thickness: about 150 microns) with a hole having a diameter of 3 mm was stuck on the surface of the exposed enamel or dentin. The adhesive composition was first applied to the holed area with a brush, then left as it was for 30 seconds, and thereafter dried with an air syringe. After thus dried, it was not fluid. Next, the bonding material was applied over it also with a brush to form thereon a layer having a thickness of about 100 microns. Then, this was exposed to light for 20 seconds and cured, under a dental light emitter, LITEL II (from Gunma Ushio Electric). Next, a commercially-available, photopolymerizable dental composite resin, CLEARFILL AP-X (from Kuraray) was put on it, covered with a film of EVAL® (from Kuraray), and pressed against a glass slide superposed thereon. In that condition, the composition was exposed to light for 40 seconds and cured, under same light emitter as above. A stainless steel rod was attached to the cured surface with a commercially-available dental resin cement, PANAVIA 21 (from Kuraray) being disposed therebetween. In that manner, plural test pieces were prepared and left as they were for 30 minutes. Some of them were immersed in water at 37° C. for 24 hours, and their bonding strength was measured. Some others were immersed in water at 37° C. for 365 days, and their bonding strength was measured. Still others were immersed in water at 37° C. for 24 hours, then subjected to 30000 thermocycles, and their bonding strength was measured. One thermocycle comprises immersing them in cold water at 4° C. for 1 minute and then in hot water at 60° C. for 1 minute. To measure the bonding strength of the test pieces, a universal tester (from Instron) was used. At a cross head speed of 2 mm/min, the tensile bonding strength of each test piece was measured. The data of eight test pieces tested under the same condition were averaged.

Example 2

MDP (15 g, 0.047 mols), distilled water (85 g) and DMAP (7.7 g, 0.047 mols) were mixed to prepare a transparent, aqueous adhesive composition containing DMAP salt of MDP. The adhesive composition and the same bonding material as in Example 1 were tested for the bonding strength, according to the same bonding strength test method as in Example 1, and the data obtained are given in Table 1.

Example 3

MDP (15 g, 0.047 mols), distilled water (85 g) and $Na_2CO_3$ (2.5 g, 0.024 mols) were mixed to prepare a transparent, aqueous adhesive composition containing sodium salt of MDP. The adhesive composition and the same bonding material as in Example 1 were tested f or the bonding strength, according to the same bonding strength test method as in Example 1, and the data obtained are given in Table 1.

Comparative Example 1

An adhesive composition comprising MDP (15 g, 0.047 mols) and distilled water (85 g) was prepared. The adhesive composition and the same bonding material as in Example 1 were tested for the bonding strength, according to the same bonding strength test method as in Example 1, and the data obtained are given in Table 1.

Comparative Example 2

An adhesive composition comprising MDP (15 g, 0.047 mols), distilled water (42.5 g) and ethanol (42.5 g) was prepared. The adhesive composition and the same bonding material as in Example 1 were tested for the bonding strength, according to the same bonding strength test method as in Example 1, and the data obtained are given in Table 1.

Comparative Example 3

An adhesive composition comprising MDP (15 g, 0.047 mols), distilled water (42.5 g) and HEMA (42.5 g) was prepared. The adhesive composition and the same bonding material as in Example 1 were tested f or the bonding strength, according to the same bonding strength test method as in Example 1, and the data obtained are given in Table 1.

Comparative Example 4

MDP (15 g, 0.047 mols), distilled water (85 g) and $CaCO_3$ (2.3 g, 0.023 mols) were mixed to prepare an adhesive composition containing calcium salt of MDP. The adhesive composition and the same bonding material as in Example 1 were tested for the bonding strength, according to the same bonding strength test method as in Example 1, and the data obtained are given in Table 1.

Comparative Example 5

An adhesive composition comprising MDP (15 g, 0.047 mols), distilled water (85 g) and DMABAE (9.0 g, 0.047 mols) was prepared. The adhesive composition and the same bonding material as in Example 1 were tested for the bonding strength, according to the same bonding strength test method as in Example 1, and the data obtained are given in Table 1.

Comparative Example 6

Maleic acid (5.4 g, 0.047 mols), distilled water (94.6 g) and DMAP (7.7 g, 0.047 mols) were mixed to prepare an adhesive composition. The adhesive composition and the same bonding material as in Example 1 were tested for the bonding strength, according to the same bonding strength test method as in Example 1, and the data obtained are given in Table 1.

Comparative Example 7

MEP (9.8 g, 0.047 mols), distilled water (90.2 g) and DMAP (7.7 g, 0.047 mols) were mixed to prepare an adhesive composition. The adhesive composition and the same bonding material as in Example 1 were tested for the bonding strength, according to the same bonding strength test method as in Example 1, and the data obtained are given in Table 1.

|  | Blend Ratio (g) | | | | | | | | | |
|---|---|---|---|---|---|---|---|---|---|---|
| Adhesive Composition | Ex. 1 | Ex. 2 | Ex. 3 | Comp. Ex. 1 | Comp. Ex. 2 | Comp. Ex. 3 | Comp. Ex. 4 | Comp. Ex. 5 | Comp. Ex. 6 | Comp. Ex. 7 |
| Acid group-containing Polymerizable Monomers | | | | | | | | | | |
| MDP | 15 | 15 | 15 | 15 | 15 | 15 | 15 | 15 | — | — |
| maleic acid | — | — | — | — | — | — | — | — | 5.4 | — |
| MEP | — | — | — | — | — | — | — | — | — | 9.8 |
| Basic Compound | | | | | | | | | | |
| NaOH | 1.9 | — | — | — | — | — | — | — | — | — |
| DMAP | — | 7.7 | — | — | — | — | — | — | 7.7 | 7.7 |
| $Na_2CO_3$ | — | — | 2.5 | — | — | — | — | — | — | — |
| $CaCO_3$ | — | — | — | — | — | — | 2.3 | — | — | — |
| DMABAE | — | — | — | — | — | — | — | 9.0 | — | — |
| Water distilled water | 85 | 85 | 85 | 85 | 42.5 | 42.5 | 85 | 85 | 94.6 | 90.2 |
| Organic Solvent ethanol | — | — | — | — | 42.5 | — | — | — | — | — |
| Hydrophilic Polymerizable Monomer HEMA | — | — | — | — | — | 42.5 | — | — | — | — |
| pH | 3.8 | 4.2 | 3.8 | 1.4 | 1.8 | 1.4 | 3.0 | 2.0 | 3.6 | 3.8 |
| Appearances | transparent | transparent | transparent | cloudy | transparent | transparent | cloudy | cloudy | transparent | transparent |
| Tensile Bonding Strength (MPa) | | | | | | | | | | |
| after 24 hours in water at 37° C.  enamel | 19.1 | 19.2 | 19.0 | 12.1 | 18.4 | 20.1 | 6.0 | 14.1 | 7.6 | 12.1 |
| dentin | 18.1 | 18.1 | 18.0 | 7.1 | 10.1 | 19.5 | 3.2 | 5.1 | 4.1 | 8.1 |
| after 365 days in water at 37° C.  enamel | 18.1 | 18.6 | 18.1 | 9.1 | 15.3 | 13.1 | 4.1 | 11.1 | 6.7 | 7.2 |
| dentin | 17.8 | 17.7 | 17.5 | 4.1 | 7.1 | 12.9 | 2.1 | 3.1 | 3.1 | 4.1 |
| after 30000 thermocycles  enamel | 18.0 | 18.2 | 18.0 | 8.5 | 14.5 | 10.1 | 3.1 | 10.1 | 6.1 | 6.9 |
| dentin | 17.6 | 17.6 | 17.6 | 3.1 | 5.1 | 9.1 | 2.1 | 2.4 | 2.9 | 3.4 |

As is clear from Table 1 above, the transparent adhesive compositions prepared by mixing a water-insoluble, acid group-containing polymerizable monomer (MDP), a basic compound and distilled water all exhibit good adhesiveness to both enamel and dentin, and have good bonding durability (Examples 1 to 3). In contrast, however, the bonding strength to a tooth of the adhesive compositions not containing the basic compound is extremely low (Comparative Examples 1 and 2). The adhesive composition containing a large amount of a hydrophilic monomer (HEMA) had extremely high bonding strength in the test where the test pieces were immersed in water at 37° C. for 1 day, but its bonding strength reduced to about a half in the test where the test pieces were immersed in water at 37° C. for 365 days and in the thermocycle test where the test pieces were subjected to 30000 thermocycles. The reduction in the boding strength of the composition is great, and this means that the bonding durability of the composition is poor (Comparative Example 3). The adhesive composition containing, as a basic compound, a salt of an alkaline earth metal and a weak acid, $CaCO_3$ formed a water-insoluble calcium salt of MDP, and its bonding strength to teeth is extremely low (Comparative Example 4). The bonding strength to teeth of the adhesive composition containing, as a basic compound, an amine, DMABAE which could not form a water-soluble salt with a water-insoluble, acid group-containing polymerizable monomer is extremely low (Comparative Example 5). The bonding strength to teeth of the adhesive composition which contains a water-soluble, acid group-containing polymeric, able monomer, maleic acid is extremely low (Comparative Example 6). The bonding strength to teeth of the adhesive composition which contains a phosphoric acid group-containing polymerizable monomer (MEP—this has two carbon atoms in the molecule) is extremely low (Comparative Example 7).

Examples 4 to 9, Comparative Examples 8 and 9

As in Table 2 below, a water-insoluble, acid group containing polymerizable monomer, a basic compound and distilled water were mixed to prepare different adhesive compositions all containing a salt of the acid group-containing polymerizable monomer but having a different pH value. Combined with the same bonding material as in Example 1, these adhesive compositions were tested for the bonding strength, according to the same bonding strength test method as in Example 1. The data obtained are given in Table 2.

|  | Blend Ratio (g) | | | | | | | |
|---|---|---|---|---|---|---|---|---|
| Adhesive Composition | Ex. 4 | Ex. 5 | Ex. 6 | Ex. 7 | Ex. 8 | Ex. 9 | Comp. Ex. 8 | Comp. Ex. 9 |
| Acid group-containing Polymerizable Monomers | | | | | | | | |
| MOTP | 30 | 30 | 30 | — | — | — | — | — |
| MDP | — | — | — | 15 | 15 | 15 | 15 | 15 |
| Basic Compound | | | | | | | | |
| $Na_2CO_3$ | 3.8 | 4.3 | 5.2 | — | — | — | 4.9 | 7.4 |
| DET | — | — | — | 2.1 | 7.0 | 11.0 | — | — |
| Water distilled water | 70 | 70 | 70 | 85 | 85 | 85 | 85 | 85 |
| pH | 1.7 | 2.1 | 2.7 | 3.5 | 4.1 | 4.9 | 7.1 | 8.2 |
| Appearances | transparent | transparent | transparent | transparent | transparent | transparent | transparent | transparent |
| Tensile Bonding Strength (MPa) | | | | | | | | |
| after 24 hours in water at 37° C. — enamel | 19.7 | 19.5 | 19.1 | 19.3 | 19.3 | 18.1 | 6.1 | 3.4 |
| after 24 hours in water at 37° C. — dentin | 17.7 | 17.9 | 17.8 | 17.6 | 17.6 | 17.5 | 4.5 | 2.1 |
| after 30000 thermocycles — enamel | 18.9 | 19.1 | 19.0 | 18.7 | 17.7 | 17.7 | 4.1 | 1.9 |
| after 30000 thermocycles — dentin | 17.4 | 17.5 | 17.8 | 17.5 | 17.0 | 17.2 | 3.1 | 1.1 |

As is clear from Table 2 above, the transparent, aqueous adhesive compositions prepared by mixing a water-insoluble, acid group-containing polymerizable monomer, a basic compound and distilled water and having pH of not larger than 5 all exhibit good adhesiveness to both enamel and dentin, and have good bonding durability (Examples 4 to 9). As opposed to these, however, the bonding strength to a tooth of the adhesive compositions having pH larger than 7 is extremely low (Comparative Examples 8 and 9).

Examples 10 to 15

As is shown in Table 3 below, MDP, DMAP and distilled water were mixed to prepare different adhesive compositions all containing DMAP salt of MDP. Combined with the same bonding material as in Example 1, these adhesive compositions were tested for the bonding strength, according to the same bonding strength test method as in Example 1. The data obtained are given in Table 3.

Comparative Examples 10 and 11

As shown in Table 3, MDP and distilled water were mixed to prepare different adhesive compositions. Combined with the same bonding material as in Example 1, these adhesive compositions were tested for the bonding strength, according to the same bonding strength test method as in Example 1. The data obtained are given in Table 3.

|  | Blend Ratio (g) | | | | | | | |
|---|---|---|---|---|---|---|---|---|
| Adhesive Composition | Ex. 10 | Ex. 11 | Ex. 12 | Ex. 13 | Ex. 14 | Ex. 15 | Comp. Ex. 10 | Comp Ex. 11 |
| Acid group-containing Polymerizable Monomer | | | | | | | | |
| MDP | 5 | 10 | 15 | 20 | 30 | 50 | 5 | 50 |
| Basic Compound | | | | | | | | |
| DMAP | 3 | 6 | 9 | 12 | 18 | 30 | — | — |
| Water distilled water | 95 | 90 | 85 | 80 | 70 | 50 | 95 | 50 |
| pH | 4.7 | 4.6 | 4.5 | 4.4 | 4.3 | 4.1 | 1.4 | 1.2 |
| Appearances | transparent | transparent | transparent | transparent | transparent | transparent | cloudy | cloudy |
| Tensile Bonding Strength (MPa) | | | | | | | | |
| after 24 hours in water at 37° C. — enamel | 14.2 | 15.1 | 18.8 | 19.1 | 19.1 | 17.5 | 6.9 | 13.0 |
| after 24 hours in water at 37° C. — dentin | 15.5 | 15.6 | 18.5 | 18.9 | 18.8 | 16.5 | 3.5 | 80 |
| after 30000 thermocycles — enamel | 14.1 | 15.2 | 18.3 | 18.5 | 18.5 | 17.3 | 6.1 | 9.8 |
| after 30000 thermocycles — dentin | 15.0 | 15.1 | 18.1 | 18.2 | 18.0 | 16.6 | 2.1 | 6.0 |

As is clear from Table 3 above, the adhesive compositions prepared by mixing MDP, DMAP and distilled water all exhibit good adhesiveness to both enamel and dentin, and have good bonding durability (Examples 10 to 15). In contrast, however, the bonding strength to a tooth of the adhesive compositions not containing DMAP is extremely low (Comparative Examples 10 and 11).

Examples 16 to 19

As shown in Table 4 below, a water-insoluble, acid group containing polymerizable monomer, a basic compound and distilled water were mixed to prepare different transparent, aqueous adhesive compositions all containing a salt of the acid group-containing polymerizable monomer. On the other hand, a bonding material comprising UDMA (65 parts by weight), 9G (30 parts by weight), MDP (5 parts by weight), CQ (1 part by weight), DMAB (1 part by weight) and BHT (0.05 parts by weight) was prepared. Combined with the bonding material, the adhesive compositions were tested for the bonding strength, according to the same bonding strength test method as in Example 1. The data obtained are given in Table 4.

Comparative Examples 12 to 15

As is shown in Table 4, a water-insoluble, acid group-containing polymerizable monomer, a basic compound, distilled water and HEMA were mixed to prepare different adhesive compositions. Combined with the same bonding material as in Example 16, these adhesive compositions were tested for the bonding strength, according to the same bonding strength test method as in Example 1. The data obtained are given in Table 4.

Example 20 and Comparative Example 16

To the adhesive composition of Example 1, were added TMPN (0.5 g) and DMAEMA (0.5 g) both serving as a polymerization initiator, to prepare a different adhesive composition. This was combined with the same bonding material as in Example 1, and tested for its bonding strength according to the same bonding strength test as in Example 1. After 30000 thermocycles, the bonding strength of the composition was 18.0 MPa to enamel and 17.7 MPa to dentin. From this, it is understood that the adhesive composition has good bonding durability (Example 20). On the other hand, TMPN (0.5 g) and DMAEMA (0.5 g) were added to the adhesive composition containing HEMA of Comparative Example 3. The resulting adhesive composition was subjected to the same thermocycle-test of 30000 thermocycles as herein. After the test, the bonding strength of the composition was 11.3 MPa to enamel and 11.7 MPa to dentin. From this, it is understood that the bonding durability of the composition (Comparative Example 16) is lower than that of the composition of Example 20.

| Adhesive Composition | | Blend Ratio (g) | | | | | | | |
|---|---|---|---|---|---|---|---|---|---|
| | | Ex. 16 | Ex. 17 | Ex. 18 | Ex. 19 | Comp. Ex. 12 | Comp. Ex. 13 | Comp. Ex. 14 | Comp. Ex. 15 |
| Acid group-containing Polymerizable Monomer | | 20 | — | — | — | 20 | — | — | — |
| MDPA | | — | 20 | — | — | — | 20 | — | — |
| MEPEP | | — | — | 20 | — | — | — | 20 | — |
| MPPN | | — | — | — | 20 | — | — | — | 20 |
| 4-MDT | | | | | | | | | |
| Basic Compound | | | | | | | | | |
| DET | | 10 | 10 | 10 | 10 | 10 | 10 | 10 | 10 |
| Water distilled water | | 80 | 80 | 80 | 80 | 40 | 40 | 40 | 40 |
| Hydrophillic Polymerizable Monomer HEMA | | — | — | — | — | 40 | 40 | 40 | 40 |
| pH | | 3.6 | 3.8 | 3.8 | 4.0 | 3.6 | 3.8 | 3.8 | 4.0 |
| Appearances | | transparent | transparent | transparent | transparent | transparent | transparent | transparent | transparent |
| Tensile Bonding Strength (MPa) | | | | | | | | | |
| after 24 hours in water at 37° C. | enamel | 19.1 | 18.8 | 19.3 | 13.8 | 19.1 | 19.8 | 19.5 | 14.0 |
| | dentin | 18.0 | 18.1 | 18.5 | 13.1 | 19.0 | 19.2 | 19.0 | 14.9 |
| after 30000 thermocycles | enamel | 18.2 | 18.3 | 18.9 | 12.9 | 11.5 | 12.9 | 11.6 | 8.0 |
| | dentin | 17.8 | 18.0 | 18.1 | 12.5 | 11.2 | 10.1 | 10.1 | 7.3 |

As clear shown in Table 4 above, the adhesive compositions prepared by mixing a substantially water-insoluble, acid group-containing polymerizable monomer, a basic compound (DET) and distilled water all exhibit good adhesiveness to both enamel and dentin, and have good bonding durability as their bonding strength was substantially maintained even after 30000 thermocycles (Examples 16 to 19). On the other hand, the adhesive composition containing a large amount of a hydrophilic monomer (HEMA) had extremely high bonding strength in the test where the test pieces were immersed in water at 37° for 1 day, but their bonding strength was reduced to about half in the heat cycle test where the test pieces were subjected to 30000 thermocycles. The reduction in the boding strength of the compositions is great, and this means that the bonding durability of the compositions is poor (Comparative Examples 12 to 15).

Example 21 and Comparative Example 17

A substantially water-insoluble, acid group-containing polymerizable monomer MEPP (15 g, 0.056 mols), a basic compound KHCO3 (5.6 g, 0.056 mols) and distilled water (85 g) were mixed to prepare an aqueous composition containing potassium salt of MEPP. To this was added methacrylic acid (5 g) serving as a pH controlling agent, to prepare a transparent adhesive composition having pH of 3.2. This was combined with the same bonding material as in Example 1, and tested for its bonding strength according to the same bonding strength test method as in Example 1. After 30000 thermocycles, the bonding strength of the composition was 15.0 MPa to enamel and 14.7 MPa to dentin. From this, it is understood that the adhesive composition has good bonding durability (Example 21). On the other hand, the adhesive composition prepared in the same manner as in the above example, to which, however, the pH controlling agent, methacrylic acid was not added and which therefore had pH of 7.8 was tested for its bonding strength in the same manner. After the heat cycle test of 30000 thermocycles, the bonding strength of the composition was 1.3 MPa to enamel and 0.7 MPa to dentin, and was extremely low (Comparative Example 17).

As described herein with reference to its preferred embodiments, the substantially transparent, adhesive composition of the invention, which contains a specific, water-insoluble, acid group-containing polymerizable monomer and/or its salt, and water and has pH falling between 1.0 and 6.0, ensures good adhesiveness between a tooth and a dental resin material, especially good bonding durability therebetween.

While the invention has been described in detail and with reference to specific embodiments thereof, it will be apparent to one skilled in the art that various changes and modifications can be made therein without departing from the spirit and scope thereof.

What is claimed is:

1. A substantially transparent adhesive composition, consisting essentially of
    (a) a substantially water-insoluble, acid group-containing polymerizable monomer, which contains in its molecule at least one hydrocarbon group selected from the group consisting of an alkylene group having from 8 to 25 carbon atoms, an alkyl group having from 8 to 25 carbon atoms, an aromatic group and a salt thereof, and
    (b) water, and
    wherein said composition has pH of from 1.0 to 6.0.

2. The adhesive composition as claimed in claim 1, wherein the acid group-containing polymerizable monomer is a di-acidic or higher poly-acidic polymerizable monomer.

3. The adhesive composition as claimed in claim 1, which has pH of from 1.5 to 5.0.

4. The adhesive composition as claimed in claim 1, further consisting essentially of a polymerization initiator.

5. The adhesive composition as claimed in claim 1, which is in the absence of a hydrophilic polymerizable monomer.

6. The adhesive composition as claimed in claim 1, wherein the acid group-containing polymerizable monomer is selected from the group consisting of a phosphoric acid group-containing polymerizable monomer, a pyrophosphoric acid group-containing polymerizable monomer, a thiophosphoric acid group-containing polymerizable monomer, a carboxylic acid group-containing polymerizable monomer and a sulfonic acid group-containing polymerizable monomer.

7. The adhesive composition as claimed in claim 1, wherein the acid group-containing polymerizable monomer is selected from the group consisting of 8-(meth)acryloyloxyoctyl dihydrogenphosphate, 9-(meth)acryloyloxynonyl dihydrogenphosphate, 10-(meth)acryloyloxydecyl dihydrogenphosphate, 11-(meth)acryloyloxyundecyl dihydrogenphosphate, 12-(meth)acryloyloxydodecyl dihydrogenphosphate, 16-(meth)acryloyloxyhexadecyl dihydrogenphosphate, 20-(meth)acryloyloxyeicosyl dihydrogenphosphate, di(meth)acryloyloxyoctyl hydrogenphosphate, di(meth)acryloyloxynonyl hydrogenphosphate, di(meth)acryloyloxydecyl hydrogenphosphate, 2-(meth)acryloyloxyethylphenyl hydrogenphosphate, 2-(meth)acryloyloxyethyl(2'-bromooctyl) hydrogenphosphate, 2-(meth)acryloyloxyethyloctyl hydrogenphosphate, 2-(meth)acryloyloxyethylnonyl hydrogenphosphate, 2-(meth)acryloyloxyethyldecyl hydrogenphosphate, 2-(meth)acryloyloxybutyldecyl hydrogenphosphate, (meth)acryloyloxyethylphenyl phosphonate, (8-methacryloxy)octyl-3-phosphonopropionate, (9-methacryloxy)nonyl-3-phosphonopropionate, (10-methacryloxy)decyl-3-phosphonopropionate, (8-methacryloxy)octyl-3-phosphonoacetate, (10-methacryloxy)decyl-3-phosphonoacetate, 2-methacryloyloxyethyl(4-methoxyphenyl) hydrogenphosphate and 2-methacryloyloxypropyl(4-methoxyphenyl) hydrogenphosphate.

8. The adhesive composition as claimed in claim 1, wherein the acid group-containing polymerizable monomer is selected from the group consisting of di(8-(meth)acryloyloxyoctyl) pyrophosphate, di(9-(meth)acryloyloxynonyl) pyrophosphate, di(10-(meth)acryloyloxydecyl) pyrophosphate, di(12-(meth)acryloyloxydodecyl) pyrophosphate and an acid chloride thereof.

9. The adhesive composition as claimed in claim 1, wherein the acid group-containing polymerizable monomer is selected from the group consisting of 8-(meth)acryloyloxyoctyl dihydrogendithiophophate, 9-(meth)acryloyloxynonyl dihydrogendithiophosphate, 10(meth)acryloyloxydecyl dihydrogenthiophosphate and an acid chloride thereof.

10. The adhesive composition as claimed in claim 1, wherein the acid group-containing polymerizable monomer is selected from the group consisting of 4-(meth)acryloyloxyethyloxycarbonylphthalic acid, 4-(meth)acryloyloxybutyloxycarbonylphthalic acid, 4-(meth)acryloyloxyhexyloxycarbonylphthalic acid, 4-(meth)acryloyloxyoctyloxycarbonylphthalic acid, 4-(meth)acryloyloxydecyloxycarbonylphthalic acid, 8-(meth)acryloylaminooctylcarboxylic acid, 9-(meth)acryloyloxy-1,1-nonane-dicarboxylic acid, 10-(meth)acryloyloxy-1,1-decane-dicarboxylic acid, 1,1-(meth)acryloyloxy-1,1-undecane-dicarboxylic acid and an acid chloride thereof.

11. The adhesive composition as claimed in claim 1, wherein the acid group-containing polymerizable monomer is selected from the group consisting of 8-(meth)acrylamidooctylsulfonic acid, 10-(meth) acrylamidodecyl-sulfonic acid and styrenesulfonic acid.

12. A method for producing a substantially transparent adhesive composition, comprising: mixing
    (a) a substantially water-insoluble, acid group-containing polymerizable monomer which contains in the molecule, at least one hydrocarbon group selected from the group consisting of an alkylene group having from 8 to 25 carbon atoms, an alkyl group having from 8 to 25 carbon atoms and an aromatic group;
    (b) a basic compound capable of forming a water-soluble salt with the acid group-containing polymerizable monomer; and
    (c) water to obtain a mixture having pH of from 1.0 to 6.0.

13. The method as claimed in claim 12, wherein said basic compound is selected from the group consisting of alkali metal hydroxide, sodium carbonate, sodium hydrogencarbonate, potassium carbonate, potassium hydrogencarbonate, lithium carbonate, lithium hydrogencarbonate, sodium formate, sodium benzoate, sodium hydrogenoxalate, sodium acetate, potassium acetate, sodium propionate, sodium borate, sodium dihydrogenphosphite, potassium dihydrogenphosphite, sodium dihydrogenphosphate, potassium dihydrogenphosphate, disodium hydrogenphosphate, dipotassium hydrogenphosphate and an amine.

14. The method as claimed in claim 13, wherein said amine is selected from the group consisting of a primary amine, a secondary amine and a tertiary amine.

15. The method as claimed in claim 13, wherein said amine is selected from the group consisting of triethanolamine, diethanolamine, 2-dimethylaminoethyl (meth)acrylate, 3-dimethylaminopropyl (meth)acrylate, 4-dimethylaminobutyl (meth)acrylate, 6-dimethylaminohexyl (meth)acrylate, 10-dimethylaminodecyl (meth)acrylate, 4-(dimethylamino) phenethyl alcohol, 4-(diethylamino) phenethyl alcohol, 4-(dipropylamino)phenethyl alcohol, N,N-(2-hydroxyethyl)-p-toluidine, N,N-(2-hydroxypropyl)-p-toluidine, diethyl-p-toluidine, dipropyl-p-toluidine, dibutyl-p-toluidine, diethoxyethyl-p-toluidine, dibutoxyethyl-p-toluidine, di(polyoxyethylene)oxyethyl-p-toluidine, hexamethylenediamine, aqueous dimethylamine, pentamethylenediamine, diethylamine, ethylenediamine, 2-aminoethanol, diethylamine and 2-dimethylaminoethanol.

16. The adhesive composition as claimed in claim 1, wherein the acid group-containing polymerizable monomer and its salt is present in an amount of from 1 wt % to 80 wt % based on the total amount of the composition.

17. The adhesive composition as claimed in claim 1, wherein the acid group-containing polymerizable monomer is present in an amount of from 5 wt % to 50 wt % based on the total amount of the composition.

18. The adhesive composition as claimed in claim 1, wherein the acid group-containing polymerizable monomer and its salt is present in an amount of from 15 wt % to 30 wt % based on the total amount of the composition.

19. The adhesive composition as claimed in claim 1, wherein the water is present in an amount of from 1 wt % to 99 wt %, based on the total composition.

20. The method according to claim 12, wherein no organic solvent is added.

21. A substantially transparent adhesive composition obtained by mixing
   (a) a substantially water-insoluble, acid group-containing polymerizable monomer which contains in the molecule, at least one hydrocarbon group selected from the group consisting of an alkylene group having from 8 to 25 carbon atoms, an alkyl group having from 8 to 25 carbon atoms and an aromatic group;
   (b) a basic compound capable of forming a water-soluble salt with the acid group-containing polymerizable monomer; and
   (c) water to obtain a mixture having pH of from 1.0 to 6.0; wherein no organic solvent is added.

* * * * *